United States Patent [19]
O'Hara et al.

[11] Patent Number: 5,952,011
[45] Date of Patent: Sep. 14, 1999

[54] HUMAN TRANSGLUTAMINASES

[75] Inventors: Patrick J. O'Hara; Francis J. Grant, both of Seattle; Paul O. Sheppard, Redmond, all of Wash.

[73] Assignee: ZymoGenetics, Inc., Seattle, Wash.

[21] Appl. No.: 08/452,800

[22] Filed: May 30, 1995

Related U.S. Application Data

[60] Division of application No. 07/998,973, Dec. 30, 1992, Pat. No. 5,514,579, which is a continuation-in-part of application No. 07/816,284, Dec. 31, 1991, abandoned.

[51] Int. Cl.$^6$ .............................. A61K 38/51; C12N 9/10; C07H 21/04
[52] U.S. Cl. ......................... 424/945; 435/193; 536/23.2
[58] Field of Search .................................. 435/69.1, 69.2, 435/193, 240.2, 254.3, 320.1; 536/23.2, 24.31; 424/94.5

[56] References Cited

U.S. PATENT DOCUMENTS

| | | | |
|---|---|---|---|
| 4,683,202 | 7/1987 | Mullis | 435/91.2 |
| 4,686,195 | 8/1987 | Mullis et al. | 501/12 |
| 4,769,328 | 9/1988 | Murray et al. | 435/69.1 |
| 5,075,227 | 12/1991 | Hagen | 435/91.41 |

FOREIGN PATENT DOCUMENTS

| | | |
|---|---|---|
| 236978 | 9/1987 | European Pat. Off. . |
| 278416 | 8/1988 | European Pat. Off. . |
| 91-06553 | 5/1991 | WIPO . |

OTHER PUBLICATIONS

Dubbink et al. "Tissue–Specific and androgen–regulated . . . " Biochem J. (1996) 315: pp. 901–908.

Folk, "Transglutaminases", *Ann. Rev. Biochem.* 49: 517–531 (1980).

Bures et al., "Transglutaminase Activity of Cultured Human Prostatic Epithelium" *Biol. Abst.* 70:3588 (1980).

Lee et al., "Purification of Human Erthrocyte Transglutaminase by Immunoaffinity Chromatography", *Prep. Biochem.* 16:321–335 (1986).

Ichinose et al., "Amino Acid Sequence of the A Subunit of Human Factor XIII", *Biochem.* 25: 6900–6906 (1986).

Grundmann et al., "Characterization of cDNA Coding for Human Factor XIIIa", *Proc. Natl. Acad. Sci. USA* 83: 8024–8028 (Nov., 1986).

Takahashi et al., "Primary Structure of Blood Coagulation Faction XIIIa (fibrinoligase, transglutaminase) from Human Placenta", *Proc. Natl. Acad. Sci. USA* 83: 8018–8023 (Nov., 1986).

Ablin et al., "Transglutaminase in the Human Prostate and Seminal Plasma: Identification and Possible Implications", *Proc. Am. Assoc. Cancer Res. Annual. Meeting* 28:174 (1987).

Ablin et al., "Identification of Transglutaminase in Human Prostate and Seminal Plasma", *Fed Proc.* 46:1495 (1987).

Ho et al., "Androgen Regulated Prostate Genes: Stuctural Analysis and Regulation", *Prog. Clin Biol. Res.* 239:125–133, (1987).

Ikura et al., "Amino Acid Sequence of Guinea Pig Liver Transglutaminase from its cDNA Sequence", *Biochem.* 27:2898–2905 (1988).

Ichinose and Davie, "Characterization of the Gene for the A Subunit of Human Factor XIII (Plasma Transglutaminase), a Blood Coagulation Factor", *Proc. Natl. Acad. Sci. USA* 85:5829–5833 (Aug. 1988).

Aumuller et al., "Differential Reaction of Secretory and Non–secretory Proteins in Hormone–Treated Dunning Tumor", *The Prostate* 15:81–94 (1989).

Floyd and Jetten, "Regulation of Type I (Epidermal) Transglutaminase mRNA Levels During Squamous Differentiation: Down Regulation By Retinoids", *Mol. Cell. Biol.* 9:4846–4851 (Nov., 1989).

Seitz et al., "Immunohistochemistry of Secretory Transglutaminase from Rodent Prostate", *Histochemistry* 93:525–530 (1990).

Enderle–Schmitt et al., "Specific Proteins of the Prostate" *Mammalian Biochem. Abst.* 112:95963j (1990).

Phillips et al., "Primary Structure of Keratinocyte Transglutaminase", *Proc. Natl. Acad. Sci. USA* 87:9333–9337 (Dec. 1990).

Gentile et al., "Isolation and Characterization of cDNA Clones to Mouse Macrophage and Human Endothelial Cell Tissue Transglutaminases"*J. Biol. Chem.* 1:478–483 (Jan. 5, 1991).

Seitz et al., "Purification and Molecular Characterization of a Secretory Tranglutaminase from Coagulating Gland of the Rat", *Biochem. Biophys. Acta* 1078:139–146 (1991).

Yamanishi et al., "Molecular Cloning of Human Epidermal Transglutaminase cDNA from Keratinocytes in Culture" *Biochem. Biophy. Res. Comm.* 175:906–913 (Mar. 19, 1991).

*Primary Examiner*—Robert A. Wax
*Assistant Examiner*—Elizabeth Slobodyansky
*Attorney, Agent, or Firm*—Townsend and Townsend and Crew LLP

[57] ABSTRACT

Human prostatic and placental transglutaminases are identified and cloned. The human transglutaminases herein are useful for, inter alia, therapeutic wound repair, closure of skin grafts, stabilizing food preparations, and markers for identifying agents which act as agonists or antagonists of cellular apoptosis.

4 Claims, No Drawings

```
                         SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (vii) IMMEDIATE SOURCE:
         (B) CLONE: ZC4109

(xi) SEQUENCE DESCRIPTION: SEQ ID NO:1:

TAYGGNCART GYTGGGTNTT                                                          20

(2) INFORMATION FOR SEQ ID NO:2:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (vii) IMMEDIATE SOURCE:
         (B) CLONE: ZC4110

(xi) SEQUENCE DESCRIPTION: SEQ ID NO:2:

GARTAYSTNC TNAMNSA                                                             17

(2) INFORMATION FOR SEQ ID NO:3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (vii) IMMEDIATE SOURCE:
         (B) CLONE: ZC4111

(xi) SEQUENCE DESCRIPTION: SEQ ID NO:3:

CCYTCNKGRW RYTTRTA                                                             17

(2) INFORMATION FOR SEQ ID NO:4:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (vii) IMMEDIATE SOURCE:
         (B) CLONE: ZC4112

(xi) SEQUENCE DESCRIPTION: SEQ ID NO:4:

AANACCCARC AYTGNCC                                                             17
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC4120

(xi) SEQUENCE DESCRIPTION: SEQ ID NO:5:

CATCCACGGA CTACGACGAR TAYSTNCTNA MYGA                34

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC4121

(xi) SEQUENCE DESCRIPTION: SEQ ID NO:6:

CATCCACGGA CTACGACGAR TAYSTNCTNA MRGA                34

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC4122

(xi) SEQUENCE DESCRIPTION: SEQ ID NO:7:

CATCCACGGA CTACGACGAR TAYSTNCTNA MNCA                34

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (vii) IMMEDIATE SOURCE:
        (B) CLONE: ZC4127

(xi) SEQUENCE DESCRIPTION: SEQ ID NO:8:

CATCCACGGA CTACGACTAY GGNCARTGYT GGGTNTT              37

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC4128

(xi) SEQUENCE DESCRIPTION: SEQ ID NO:9:

ACTCTCCGGT ACGACAGAAN ACCCARCAYT GNCC                34

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC4129

(xi) SEQUENCE DESCRIPTION: SEQ ID NO:10:

```
ACTCTCCGGT ACGACAGCCY TCNKGRWRYT TRTA                                       34
```

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (vii) IMMEDIATE SOURCE:
        (B) CLONE: ZC4248

(xi) SEQUENCE DESCRIPTION: SEQ ID NO:11:

```
AGAGGCGATA TCTCTCCGCC TGTCTTGGCC CACTGC                                     36
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (vii) IMMEDIATE SOURCE:
        (B) CLONE: ZC4249

(xi) SEQUENCE DESCRIPTION: SEQ ID NO:12:

```
GGGATCCTGA CTACAGTGCT GAGAGCGTTG GGCATC                                     36
```

(2) INFORMATION FOR SEQ ID NO:13:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (vii) IMMEDIATE SOURCE:
        (B) CLONE: PTG562

(xi) SEQUENCE DESCRIPTION: SEQ ID NO:13:

```
TATGGACAGT GCTGGGTATT TGCTGGGATC CTGACTACAG TGCTGAGAGC GTTGGGCATC           60
CCAGCACGCA GTGTGACAGG CTTCGATTCA GCTCACGACA CAGAAAGGAA CCTCACGGTG          120
GACACCTATG TGAATGAGAA TGGCGAGAAA ATCACCAGTA TGACCCACGA CTCTGTCTGG          180
AATTTCCATG TGTGGACGGA TGCCTGGATG AAGCGACCCT ACGACGGCTG GCAGGCTGTG          240
GACGCAACGC CGCAGGAGCG AAGCCAGGGT GTCTTCTGCT GTGGGCCATC ACCACTGACC          300
GCCATCCGCA AAGGTGACAT CTTTATTGTC TATGACACCA GATTCGTCTT CTCAGAAGTG          360
AATGGTGACA GGCTCATCTG GTTGGTGAAG ATGGTGAATG GCAGGAGGA GTTACACGTA           420
ATTTCAATGG AGACCACAAG CATCGGGAAA ACATCAGCA CCAAGGCAGT GGGCCAAGAC           480
AGGCGGAGAG ATATCGCCTC TGAGTACAAG CTCCCCGAAG G                              521
```

(2) INFORMATION FOR SEQ ID NO:14:

(i) SEQUENCE CHARACTERISTICS:
      (A) LENGTH: 3064 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 147..2186

(xi) SEQUENCE DESCRIPTION: SEQ ID NO:14:

```
AATTCTAAAA ATGCTTTTGC AAGCTTGCAT GCCTGCAGGT GCAGCGGCCG CCAGTGTGAT        60

GGATATCTGC AGAATTCGGC TTGCGCTCAG CTGGAATTCC GCAGAGATAG AGTCTTCCCT       120

GGCATTGCAG AGAGAATCT GAAGGG ATG ATG GAT GCA TCA AAA GAG CTG CAA        173
                            Met Met Asp Ala Ser Lys Glu Leu Gln
                              1               5

GTT CTC CAC ATT GAC TTC TTG AAT CAG GAC AAC GCC GTT TCT CAC CAC        221
Val Leu His Ile Asp Phe Leu Asn Gln Asp Asn Ala Val Ser His His
 10              15                  20                  25

ACA TGG GAG TTC CAA ACG AGC AGT CCT GTG TTC CGG CGA GGA CAG GTG        269
Thr Trp Glu Phe Gln Thr Ser Ser Pro Val Phe Arg Arg Gly Gln Val
                 30                  35                  40

TTT CAC CTG CGG CTG GTG CTG AAC CAG CCC CTA CAA TCC TAC CAC CAA        317
Phe His Leu Arg Leu Val Leu Asn Gln Pro Leu Gln Ser Tyr His Gln
             45                  50                  55

CTG AAA CTG GAA TTC AGC ACA GGG CCG AAT CCT AGC ATC GCC AAA CAC        365
Leu Lys Leu Glu Phe Ser Thr Gly Pro Asn Pro Ser Ile Ala Lys His
         60                  65                  70

ACC CTG GTG GTG CTC GAC CCG AGG ACG CCC TCA GAC CAC TAC AAC TGG        413
Thr Leu Val Val Leu Asp Pro Arg Thr Pro Ser Asp His Tyr Asn Trp
 75                  80                  85

CAG GCA ACC CTT CAA AAT GAG TCT GGC AAA GAG GTC ACA GTG GCT GTC        461
Gln Ala Thr Leu Gln Asn Glu Ser Gly Lys Glu Val Thr Val Ala Val
 90                  95                 100                 105

ACC AGT TCC CCC AAT GCC ATC CTG GGC AAG TAC CAA CTA AAC GTG AAA        509
Thr Ser Ser Pro Asn Ala Ile Leu Gly Lys Tyr Gln Leu Asn Val Lys
                110                 115                 120

ACT GGA AAC CAC ATC CTT AAG TCT GAA GAA AAC ATC CTA TAC CTT CTC        557
Thr Gly Asn His Ile Leu Lys Ser Glu Glu Asn Ile Leu Tyr Leu Leu
            125                 130                 135

TTC AAC CCA TGG TGT AAA GAG GAC ATG GTT TTC ATG CCT GAT GAG GAC        605
Phe Asn Pro Trp Cys Lys Glu Asp Met Val Phe Met Pro Asp Glu Asp
        140                 145                 150

GAG CGC AAA GAG TAC ATC CTC AAT GAC ACG GGC TGC CAT TAC GTG GGG        653
Glu Arg Lys Glu Tyr Ile Leu Asn Asp Thr Gly Cys His Tyr Val Gly
    155                 160                 165

GCT GCC AGA AGT ATC AAA TGC AAA CCC TGG AAC TTT GGT CAG TTT GAG        701
Ala Ala Arg Ser Ile Lys Cys Lys Pro Trp Asn Phe Gly Gln Phe Glu
170                 175                 180                 185

AAA AAT GTC CTG GAC TGC TGC ATT TCC CTG CTG ACT GAG AGC TCC CTC        749
Lys Asn Val Leu Asp Cys Cys Ile Ser Leu Leu Thr Glu Ser Ser Leu
                190                 195                 200

AAG CCC ACA GAT AGG AGG GAC CCC GTG CTG GTG TGC AGG GCC ATG TGT        797
Lys Pro Thr Asp Arg Arg Asp Pro Val Leu Val Cys Arg Ala Met Cys
            205                 210                 215

GCT ATG ATG AGC TTT GAG AAA GGC CAG GGC GTG CTC ATT GGG AAT TGG        845
Ala Met Met Ser Phe Glu Lys Gly Gln Gly Val Leu Ile Gly Asn Trp
        220                 225                 230
```

|     |     |
| --- | --- |
| ACT GGG GAC TAC GAA GGT GGC ACA GCC CCA TAC AAG TGG ACA GGC AGT<br>Thr Gly Asp Tyr Glu Gly Gly Thr Ala Pro Tyr Lys Trp Thr Gly Ser<br>235                    240                    245 | 893 |
| GCC CCG ATC CTG CAG CAG TAC TAC AAC ACG AAG CAG GCT GTG TGC TTT<br>Ala Pro Ile Leu Gln Gln Tyr Tyr Asn Thr Lys Gln Ala Val Cys Phe<br>250                    255                    260                    265 | 941 |
| GGC CAG TGC TGG GTG TTT GCT GGG ATC CTG ACT ACA GTG CTG AGA GCG<br>Gly Gln Cys Trp Val Phe Ala Gly Ile Leu Thr Thr Val Leu Arg Ala<br>                  270                    275                    280 | 989 |
| TTG GGC ATC CCA GCA CGC AGT GTG ACA GGC TTC GAT TCA GCT CAC GAC<br>Leu Gly Ile Pro Ala Arg Ser Val Thr Gly Phe Asp Ser Ala His Asp<br>                  285                    290                    295 | 1037 |
| ACA GAA AGG AAC CTC ACG GTG GAC ACC TAT GTG AAT GAG AAT GGC GAG<br>Thr Glu Arg Asn Leu Thr Val Asp Thr Tyr Val Asn Glu Asn Gly Glu<br>300                    305                    310 | 1085 |
| AAA ATC ACC AGT ATG ACC CAC GAC TCT GTC TGG AAT TTC CAT GTG TGG<br>Lys Ile Thr Ser Met Thr His Asp Ser Val Trp Asn Phe His Val Trp<br>315                    320                    325 | 1133 |
| ACG GAT GCC TGG ATG AAG CGA CCC TAC GAC GGC TGG CAG GCT GTG GAC<br>Thr Asp Ala Trp Met Lys Arg Pro Tyr Asp Gly Trp Gln Ala Val Asp<br>330                    335                    340                    345 | 1181 |
| GCA ACG CCG CAG GAG CGA AGC CAG GGT GTC TTC TGC TGT GGG CCA TCA<br>Ala Thr Pro Gln Glu Arg Ser Gln Gly Val Phe Cys Cys Gly Pro Ser<br>                  350                    355                    360 | 1229 |
| CCA CTG ACC GCC ATC CGC AAA GGT GAC ATC TTT ATT GTC TAT GAC ACC<br>Pro Leu Thr Ala Ile Arg Lys Gly Asp Ile Phe Ile Val Tyr Asp Thr<br>                  365                    370                    375 | 1277 |
| AGA TTC GTC TTC TCA GAA GTG AAT GGT GAC AGG CTC ATC TGG TTG GTG<br>Arg Phe Val Phe Ser Glu Val Asn Gly Asp Arg Leu Ile Trp Leu Val<br>                      380                    385                    390 | 1325 |
| AAG ATG GTG AAT GGG CAG GAG GAG TTA CAC GTA ATT TCA ATG GAG ACC<br>Lys Met Val Asn Gly Gln Glu Glu Leu His Val Ile Ser Met Glu Thr<br>395                    400                    405 | 1373 |
| ACA AGC ATC GGG AAA AAC ATC AGC ACC AAG GCA GTG GGC CAA GAC AGG<br>Thr Ser Ile Gly Lys Asn Ile Ser Thr Lys Ala Val Gly Gln Asp Arg<br>410                    415                    420                    425 | 1421 |
| CGG AGA GAT ATC ACC TAT GAG TAC AAG TAT CCA GAA GGC TCC TCT GAG<br>Arg Arg Asp Ile Thr Tyr Glu Tyr Lys Tyr Pro Glu Gly Ser Ser Glu<br>                      430                    435                    440 | 1469 |
| GAG AGG CAG GTC ATG GAT CAT GCC TTC CTC CTT CTC AGT TCT GAG AGG<br>Glu Arg Gln Val Met Asp His Ala Phe Leu Leu Leu Ser Ser Glu Arg<br>                  445                    450                    455 | 1517 |
| GAG CAC AGA CAG CCT GTA AAA GAG AAC TTT CTT CAC ATG TCG GTA CAA<br>Glu His Arg Gln Pro Val Lys Glu Asn Phe Leu His Met Ser Val Gln<br>                  460                    465                    470 | 1565 |
| TCA GAT GAT GTG CTG CTG GGA AAC TCT GTT AAT TTC ACC GTG ATT CTT<br>Ser Asp Asp Val Leu Leu Gly Asn Ser Val Asn Phe Thr Val Ile Leu<br>475                    480                    485 | 1613 |
| AAA AGG AAG ACC GCT GCC CTA CAG AAT GTC AAC ATC TTG GGC TCC TTT<br>Lys Arg Lys Thr Ala Ala Leu Gln Asn Val Asn Ile Leu Gly Ser Phe<br>490                    495                    500                    505 | 1661 |
| GAA CTA CAG TTG TAC ACT GGC AAG AAG ATG GCA AAA CTG TGT GAC CTC<br>Glu Leu Gln Leu Tyr Thr Gly Lys Lys Met Ala Lys Leu Cys Asp Leu<br>                  510                    515                    520 | 1709 |
| AAT AAG ACC TCG CAG ATC CAA GGT CAA GTA TCA GAA GTG ACT CTG ACC<br>Asn Lys Thr Ser Gln Ile Gln Gly Gln Val Ser Glu Val Thr Leu Thr<br>                      525                    530                    535 | 1757 |
| TTG GAC TCC AAG ACC TAC ATC AAC AGC CTG GCT ATA TTA GAT GAT GAG<br>Leu Asp Ser Lys Thr Tyr Ile Asn Ser Leu Ala Ile Leu Asp Asp Glu<br>                  540                    545                    550 | 1805 |

```
CCA GTT ATC AGA GGT TTC ATC ATT GCG GAA ATT GTG GAG TCT AAG GAA    1853
Pro Val Ile Arg Gly Phe Ile Ile Ala Glu Ile Val Glu Ser Lys Glu
        555                 560                 565

ATC ATG GCC TCT GAA GTA TTC ACG TCA AAC CAG TAC CCT GAG TTC TCT    1901
Ile Met Ala Ser Glu Val Phe Thr Ser Asn Gln Tyr Pro Glu Phe Ser
570                 575                 580                 585

ATA GAG TTG CCT AAC ACA GGC AGA ATT GGC CAG CTA CTT GTC TGC AAT    1949
Ile Glu Leu Pro Asn Thr Gly Arg Ile Gly Gln Leu Leu Val Cys Asn
                590                 595                 600

TGT ATC TTC AAG AAT ACC CTG GCC ATC CCT TTG ACT GAC GTC AAG TTC    1997
Cys Ile Phe Lys Asn Thr Leu Ala Ile Pro Leu Thr Asp Val Lys Phe
            605                 610                 615

TCT TTG GAA AGC CTG GGC ATC TCC TCA CTA CAG ACC TCT GAC CAT GGG    2045
Ser Leu Glu Ser Leu Gly Ile Ser Ser Leu Gln Thr Ser Asp His Gly
        620                 625                 630

ACG GTG CAG CCT GGT GAG ACC ATC CAA TCC CAA ATA AAA TGC ACC CCA    2093
Thr Val Gln Pro Gly Glu Thr Ile Gln Ser Gln Ile Lys Cys Thr Pro
635                 640                 645

ATA AAA ACT GGA CCC AAG AAA TTT ATC GTC AAG TTA AGT TCC AAA CAA    2141
Ile Lys Thr Gly Pro Lys Lys Phe Ile Val Lys Leu Ser Ser Lys Gln
650                 655                 660                 665

GTG AAA GAG ATT AAT GCT CAG AAG ATT GTT CTC ATC ACC AAG TAGCCTTGTC 2193
Val Lys Glu Ile Asn Ala Gln Lys Ile Val Leu Ile Thr Lys
                670                 675                 680

TGATGCTGTG GAGCCTTAGT TGAGATTTCA GCATTTCCTA CCTTGTGCTT AGCTTTCAGA    2253

TTATGGATGA TTAAATTTGA TGACTTATAT GAGGGCAGAT TCAAGAGCCA GCAGGTCAAA    2313

AAGGCCAACA CAACCATAAG CAGCCAGACC CACAAGGCCA GGTCCTGTGC TATCACAGGG    2373

TCACCTCTTT TACAGTTAGA AACACCAGCC GAGGCCACAG AATCCCATCC CTTTCCTGAG    2433

TCATGGCCTC AAAAATCAGG GCCACCATTG TCTCAATTCA AATCCATAGA TTTCGAAGCC    2493

ACAGAGCTCT TCCCTGGAGC AGCAGACTAT GGGCAGCCCA GTGCTGCCAC CTGCTGACGA    2553

CCCTTGAGAA GCTGCCATAT CTTCAGGCCA TGGGTTCACC AGCCCTGAAG CACCTGTCA     2613

ACTGGAGTGC TCTCTCAGCA CTGGGATGGG CCTGATAGAA GTGCATTCTC CTCCTATTGC    2673

CTCCATTCTC CTCTCTCTAT CCCTGAAATC AGGAAGTCC CTCTCCTGGT GCTCCAAGCA     2733

GTTTGAAGCC CAATCTGCAA GGACATTTCT CAAGGGCCAT GTGGTTTTGC AGACAACCCT    2793

GTCCTCAGGC CTGAACTCAC CATAGAGACC CATGTCAGCA AACGGTGACC AGCAAATCCT    2853

CTTCCCTTAT TCTAAAGCTG CCCCTTGGGA GACTCCAGGG AGAAGGCATT GCTTCCTCCC    2913

TGGTGTGAAC TCTTTCTTTG GTATTCCATC CACTATCCTG GCAACTCAAG GCTGCTTCTG    2973

TTAACTGAAG CCTGCTCCTT CTTGTTCTGC CCTCCAGAGA TTTGCTCAAA TGATCAATAA    3033

GCTTTAAATT AAACCGGAAT CCGCGGAATT C                                   3064

(2) INFORMATION FOR SEQ ID NO:15:

(i) SEQUENCE CHARACTERISTICS:
        (A) LENGTH: 679 amino acids
        (B) TYPE: amino acid
        (D) TOPOLOGY: linear (ii) MOLECULE TYPE: protein (xi) SEQUENCE DESCRIPTION: SEQ ID NO:15:

Met Met Asp Ala Ser Lys Glu Leu Gln Val Leu His Ile Asp Phe Leu
  1               5                  10                  15

Asn Gln Asp Asn Ala Val Ser His His Thr Trp Glu Phe Gln Thr Ser
             20                  25                  30
```

```
Ser Pro Val Phe Arg Arg Gly Gln Val Phe His Leu Arg Leu Val Leu
         35                  40                  45

Asn Gln Pro Leu Gln Ser Tyr His Gln Leu Lys Leu Glu Phe Ser Thr
 50                  55                  60

Gly Pro Asn Pro Ser Ile Ala Lys His Thr Leu Val Val Leu Asp Pro
 65                  70                  75                  80

Arg Thr Pro Ser Asp His Tyr Asn Trp Gln Ala Thr Leu Gln Asn Glu
                 85                  90                  95

Ser Gly Lys Glu Val Thr Val Ala Val Thr Ser Ser Pro Asn Ala Ile
                100                 105                 110

Leu Gly Lys Tyr Gln Leu Asn Val Lys Thr Gly Asn His Ile Leu Lys
                115                 120                 125

Ser Glu Glu Asn Ile Leu Tyr Leu Leu Phe Asn Pro Trp Cys Lys Glu
130                 135                 140

Asp Met Val Phe Met Pro Asp Glu Asp Glu Arg Lys Glu Tyr Ile Leu
145                 150                 155                 160

Asn Asp Thr Gly Cys His Tyr Val Gly Ala Ala Arg Ser Ile Lys Cys
                165                 170                 175

Lys Pro Trp Asn Phe Gly Gln Phe Glu Lys Asn Val Leu Asp Cys Cys
                180                 185                 190

Ile Ser Leu Leu Thr Glu Ser Ser Leu Lys Pro Thr Asp Arg Arg Asp
        195                 200                 205

Pro Val Leu Val Cys Arg Ala Met Cys Ala Met Met Ser Phe Glu Lys
        210                 215                 220

Gly Gln Gly Val Leu Ile Gly Asn Trp Thr Gly Asp Tyr Glu Gly Gly
225                 230                 235                 240

Thr Ala Pro Tyr Lys Trp Thr Gly Ser Ala Pro Ile Leu Gln Gln Tyr
                245                 250                 255

Tyr Asn Thr Lys Gln Ala Val Cys Phe Gly Gln Cys Trp Val Phe Ala
                260                 265                 270

Gly Ile Leu Thr Thr Val Leu Arg Ala Leu Gly Ile Pro Ala Arg Ser
        275                 280                 285

Val Thr Gly Phe Asp Ser Ala His Asp Thr Glu Arg Asn Leu Thr Val
        290                 295                 300

Asp Thr Tyr Val Asn Glu Asn Gly Glu Lys Ile Thr Ser Met Thr His
305                 310                 315                 320

Asp Ser Val Trp Asn Phe His Val Trp Thr Asp Ala Trp Met Lys Arg
                325                 330                 335

Pro Tyr Asp Gly Trp Gln Ala Val Asp Ala Thr Pro Gln Glu Arg Ser
                340                 345                 350

Gln Gly Val Phe Cys Cys Gly Pro Ser Pro Leu Thr Ala Ile Arg Lys
                355                 360                 365

Gly Asp Ile Phe Ile Val Tyr Asp Thr Arg Phe Val Phe Ser Glu Val
370                 375                 380

Asn Gly Asp Arg Leu Ile Trp Leu Val Lys Met Val Asn Gly Gln Glu
385                 390                 395                 400

Glu Leu His Val Ile Ser Met Glu Thr Thr Ser Ile Gly Lys Asn Ile
                405                 410                 415

Ser Thr Lys Ala Val Gly Gln Asp Arg Arg Asp Ile Thr Tyr Glu
                420                 425                 430

Tyr Lys Tyr Pro Glu Gly Ser Ser Glu Glu Arg Gln Val Met Asp His
        435                 440                 445

Ala Phe Leu Leu Leu Ser Ser Glu Arg Glu His Arg Gln Pro Val Lys
450                 455                 460
```

-continued

Glu Asn Phe Leu His Met Ser Val Gln Ser Asp Asp Val Leu Leu Gly
465                 470                 475                 480

Asn Ser Val Asn Phe Thr Val Ile Leu Lys Arg Lys Thr Ala Ala Leu
            485                 490                 495

Gln Asn Val Asn Ile Leu Gly Ser Phe Glu Leu Gln Leu Tyr Thr Gly
            500                 505                 510

Lys Lys Met Ala Lys Leu Cys Asp Leu Asn Lys Thr Ser Gln Ile Gln
            515                 520                 525

Gly Gln Val Ser Glu Val Thr Leu Thr Leu Asp Ser Lys Thr Tyr Ile
530                 535                 540

Asn Ser Leu Ala Ile Leu Asp Asp Glu Pro Val Ile Arg Gly Phe Ile
545                 550                 555                 560

Ile Ala Glu Ile Val Glu Ser Lys Glu Ile Met Ala Ser Glu Val Phe
            565                 570                 575

Thr Ser Asn Gln Tyr Pro Glu Phe Ser Ile Glu Leu Pro Asn Thr Gly
            580                 585                 590

Arg Ile Gly Gln Leu Leu Val Cys Asn Cys Ile Phe Lys Asn Thr Leu
            595                 600                 605

Ala Ile Pro Leu Thr Asp Val Lys Phe Ser Leu Glu Ser Leu Gly Ile
610                 615                 620

Ser Ser Leu Gln Thr Ser Asp His Gly Thr Val Gln Pro Gly Glu Thr
625                 630                 635                 640

Ile Gln Ser Gln Ile Lys Cys Thr Pro Ile Lys Thr Gly Pro Lys Lys
            645                 650                 655

Phe Ile Val Lys Leu Ser Ser Lys Gln Val Lys Glu Ile Asn Ala Gln
            660                 665                 670

Lys Ile Val Leu Ile Thr Lys
            675

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: ZC1157

(xi) SEQUENCE DESCRIPTION: SEQ ID NO:16:

AATTCTAAAA ATGCTTTTGC A                                               21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: ZC1158

(xi) SEQUENCE DESCRIPTION: SEQ ID NO:17:

AGCTTGCAAA AGCATTTTTA G                                               21

(2) INFORMATION FOR SEQ ID NO:18:

(i) SEQUENCE CHARACTERISTICS:
        (A) LENGTH: 15 base pairs

```
            (B) TYPE: nucleic acid
            (C) STRANDEDNESS: single
            (D) TOPOLOGY: linear (vii) IMMEDIATE SOURCE:
            (B) CLONE: ZC4048

(xi) SEQUENCE DESCRIPTION: SEQ ID NO:18:

GCGCTCAGCT GGAAT                                                         15

(2) INFORMATION FOR SEQ ID NO:19:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (vii) IMMEDIATE SOURCE:
            (B) CLONE: ZC4362

(xi) SEQUENCE DESCRIPTION: SEQ ID NO:19:

TGAATATCGA CGGTTTCCAT ATGG                                               24

(2) INFORMATION FOR SEQ ID NO:20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (vii) IMMEDIATE SOURCE:
            (B) CLONE: ZC4363

(xi) SEQUENCE DESCRIPTION: SEQ ID NO:20:

TATTTTTGAC ACCAGACCAA CTGG                                               24

(2) INFORMATION FOR SEQ ID NO:21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (vii) IMMEDIATE SOURCE:
            (B) CLONE: ZC5509

(xi) SEQUENCE DESCRIPTION: SEQ ID NO:21:

ACCATGTCCT CTTTACACCA T                                                  21

(2) INFORMATION FOR SEQ ID NO:22:

(i) SEQUENCE CHARACTERISTICS:
            (A) LENGTH: 527 base pairs
            (B) TYPE: nucleic acid
            (C) STRANDEDNESS: single
            (D) TOPOLOGY: linear (vii) IMMEDIATE SOURCE:
            (B) CLONE: p1TG (xi) SEQUENCE DESCRIPTION: SEQ ID NO:22:

TATGGTCAGT GTTGGGTTTT TGCTGGGACC CTCAACACAG CGCTGCGGTC TTTGGGGATT        60

CCTTCCCGGG TGATCACCAA CTTCAACTCA GCTCATGACA CAGACCGAAA TCTCAGTGTG       120

GATGTGTACT ACGACCCCAT GGGAAACCCC CTGGACAAGG GTAGTGATAG CGTATGGAAT       180

TTCCATGTCT GGAATGAAGG CTGGTTTGTG AGGTCTGACC TGGGCCCCTC GTACGGTGGA       240
```

```
TGGCAGGTGT TGGATGCTAC CCCGCAGGAA AGAAGCCAAG GGGTGTTCCA GTGCGGCCCC        300

GCTTCGGTCA TTGGTGTTCG AGAGGGTGAT GTGCAGCTGA ACTTCGACAT GCCCTTTATC        360

TTCGCGGAGG TTAATGCCGA CCGCATCACC TGGCTGTACG ACAACACCAC TGGCAAACAG        420

TGGAAGAATT CCGTGAACAG TCACACCATT GGCAGGTACA TCAGCACCAA GGCGGTGGGC        480

AGCAATGCTC GCATGGACGT CACGGACAAG TACAAGCTCC ACGAGGG                     527
```

HUMAN TRANSGLUTAMINASES

RELATED APPLICATION

This application is a divisional of Ser. No. 07/998,973, filed Dec. 30, 1992, now U.S. Pat. No. 5,514,579, which is a continuation-in-part of Ser. No. 07/816,284, filed Dec. 31, 1991 (now abandoned), which are incorporated herein by reference.

BACKGROUND OF THE INVENTION

Transglutaminases are a group of calcium dependent enzymes that catalyze the crosslinking of proteins by promoting the formation of ε-(γ-glutaminyl)lysine isopeptide bonds between protein-bound glutamine and lysine residues. These enzymes are believed to be widely distributed in nature, as the crosslinks are found in both prokaryotic and eukaryotic cells. Although different transglutaminases appear to be very similar in substrate specificity, several distinct forms of the enzymes have been identified. See generally, Folk, *Ann. Rev. Biochem.* 49:517–531 (1980).

Transglutaminase-mediated protein crosslinking reactions have been implicated in both normal and pathological processes in mammalian cells and tissues. The crosslink may act to maintain some forms of protein structure, such as in the terminal differentiation of epidermal cell layers and in other cellular architecture. An intracellular transglutaminase known as epidermal or Type I transglutaminase has been isolated and cloned from rabbit epithelial cells (Floyd and Jetten, *Mol. Cell. Biol.* 9:4846–4851 (1989)), and a transglutaminase has been isolated and cloned from guinea pig liver cells (Ikura et al., *Biochem.* 27: 2898–2905 (1988)). Other transglutaminase activities have been described including hair follicle transglutaminase, keratinocyte transglutaminase, and prostate transglutaminase (Wilson et al., *Fed. Proc.* 38:1809 (1979)). Lee et al., *Prep. Biochem.* 16:321–335 (1986) have described the purification of a transglutaminase from human erythrocytes. These transglutaminases have been shown to be distinct from a plasma transglutaminase, Factor XIII, an enzyme whose primary function appears to be stabilizing fibrin clots. Factor XIII has also been purified, cloned, and sequenced. (Ichinose, et al., *Biochem.* 25:6900–6906 (1986), Takahashi, et al., *Proc. Natl. Acad. Sci. U.S.A.* 83:8018–8023 (1986)).

Transglutaminases have been employed for crosslinking purposes in a variety of fields. Certain microbial transglutaminases have found use in food technology to add texture to processed foods, particularly fish and cheese. Others have been used in enzyme-catalyzed fluorescent labeling of proteins, in the introduction of cleavable crosslinks, and in the solid-phase reversible removal of specific proteins from biological systems. Factor XIII preparations have been proposed for a variety of therapeutic uses, such as the treatment of subarachnoid hemorrhage and inflammatory bowel disease.

Presently, a plasma derived Factor XIII is available as a fibrin sealant, but, as with most plasma-derived products, carries an inherent risk of viral contamination. Further, Factor XIII and certain other transglutaminases are zymogens, requiring some form of activation to become catalytically active. And, as each transglutaminase has a restricted range of substrates, their activity may be limited in certain applications. Accordingly, what is needed in the art are methods for producing by recombinant means human transglutaminases. The present invention fulfills these and other related needs.

SUMMARY OF THE INVENTION

The present invention provides the ability to produce human prostatic and placental transglutaminases and polypeptides or fragments thereof by recombinant means, preferably in cultured eukaryotic cells. The expressed transglutaminase may or may not have the biological activity of the native enzyme, depending on the intended use. Accordingly, isolated and purified polynucleotides are described which code for the transglutaminases and fragments thereof, where the polynucleotides may be in the form of DNA, such as cDNA or genomic DNA, or RNA. Based on these sequences probes may be designed for hybridization to identify these and related genes or transcription products thereof which encode human prostatic and placental transglutaminases.

In related embodiments the invention concerns DNA constructs which comprise a transcriptional promoter, a DNA sequence which encodes the prostatic or placental transglutaminase or fragment thereof, and a transcriptional terminator, each operably linked for expression of the enzyme or enzyme fragment. The constructs are preferably used to transform or transfect host cells, preferably eukaryotic cells, more preferably yeast or mammalian cells. For large scale production the expressed prostatic or placental transglutaminase may be isolated from the cells by, for example, immunoaffinity purification.

Nucleic acid sequences which encode the human prostatic or placental transglutaminases of the invention and the recombinant transglutaminases themselves can also be used to develop compounds which can alter transglutaminase-associated apoptosis of a eukaryotic cell. Compounds may be screened for agonistic or antagonistic effects on transglutaminase-mediated metabolism in the host cell.

DESCRIPTION OF THE SPECIFIC EMBODIMENTS

The present invention provides isolated polynucleotide molecules encoding human prostatic and placental transglutaminases, thereby providing for the expression of human prostatic and placental transglutaminase polypeptides and fragments thereof. Isolated polynucleotide molecules are those that are separated from their natural environment and include cDNA and genomic clones. Isolated DNA molecules of the present invention are provided free of other genes with which they are naturally associated and may include naturally occurring 5' and 3' untranslated sequences that represent regulatory regions such as promoters and terminators. The identification of regulatory regions within the naturally occurring 5' and 3' untranslated regions will be evident to one of ordinary skill in the art (for review, see Dynan and Tijan, *Nature* 316: 774–778, 1985; Birnstiel et al., *Cell* 41: 349–359, 1985; Proudfoot, *Trends in Biochem. Sci.* 14: 105–110, 1989; and Sambrook et al., *Molecular Cloning: A Laboratory Manual, Second Edition,* Cold Spring Harbor, N.Y., 1989; which are incorporated herein by reference).

As will be understood by one skilled in the art, the DNA molecules of the present invention encompass allelic variants and genetically engineered or synthetic variants of the transglutaminases that encode conservative amino acid substitutions and/or minor additions, or deletions of amino acids. Such variants also encompass DNA molecules containing degeneracies in the DNA code wherein host-preferred codons are substituted for the analogous codons in the human sequence. In addition, substantially similar DNA molecules of the present invention encompass those DNA molecules that are capable of hybridizing to the DNA sequences of the present invention under high or low stringency (see Sambrook et al., ibid.) and those sequences that are degenerate as a result of the genetic code to the amino acid sequences of the present invention.

Recombinant DNA expression systems provide convenient means for obtaining large quantities of the human transglutaminases in relatively pure form. By human prostatic or placental transglutaminase polypeptides and fragments is meant to include sequences of amino acids from 9 to 20 amino acids up to entire proteins, which have at least about 85% homology, preferably at least 90%, and more preferably at least about 95% or more homology to the amino acid sequences of the human prostatic or placental transglutaminases of the invention. As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion and insertion mutations.

Nucleic acid molecules encoding the human transglutaminases as described herein can be cloned from a variety of human cell sources that express the enzymes. Preferred sources for human prostatic transglutaminase include human prostate or liver cells and tissues, and for human placental transglutaminase include, e.g., human placental tissue. Useful isolated nucleic acid sequences of the invention which encode the human transglutaminases include mRNA, genomic DNA and cDNA. For expression, cDNAs are generally preferred because they lack introns that may interfere with expression.

To obtain human prostate and/or placental transglutaminase clones, a human prostate tissue cDNA library and/or human placental tissue cDNA library is amplified to obtain DNA molecules encoding transglutaminases using oligonucleotide primers in a polymerase chain reaction ("PCR"; U.S. Pat. Nos. 4,683,195, 4,683,202, incorporated herein by reference). The oligonucleotide primer sequences are designed by preparing a multiple sequence alignment of sequence information for a variety of transglutaminases and related proteins (e.g., rat keratinocyte transglutaminase, human keratinocyte transglutaminase, human transglutaminase K, human factor XIII, human endothelial cell transglutaminase, mouse macrophage transglutaminase, guinea pig transglutaminase, human erythrocyte membrane protein band 4.2, rabbit transglutaminase type I, and bovine factor XIII). The multiple alignment is subjected to analysis for least degenerate/most conserved regions from which primers, which are generally about 17–20 bases long, are designed. Primers were designed from three regions of multiple homology in Example I described below: one from the active site region, and two from other regions which seemed to have structural importance, based on, inter alia, the presence of hydrophobic residues and proline residues. Following amplification and enrichment for the desired DNA molecules, the molecules are identified and used to screen and isolate full length cDNA clones for the prostate and placental transglutaminases.

cDNA libraries can be screened with, e.g., labeled probes from random-primed DNA molecules encoding human prostatic or placental transglutaminase, which probes preferably span the enzyme's active site and/or putative calcium binding site. To obtain the human placental transglutaminase clone, an oligo-d(T) primed cDNA library can be constructed from poly(A)$^+$ RNA purified from human placental tissues. Partial clones may be used as probes in additional screening until the complete coding sequence is obtained.

In addition to the use of partial clones to obtain full length transglutaminase clones, PCR amplification may be used to obtain a complete cDNA. Synthetic oligonucleotide primers may be designed to hybridize to vector sequences near the cDNA insert boundary and to DNA sequences within the transglutaminase coding sequence. Polymerase chain amplification may be used in conjunction with such primers to obtain DNA segments encoding terminal DNA sequences for completing a partial cDNA clone.

If necessary, partial clones are joined in the correct reading frame to construct the complete coding sequence. Joining is achieved by, for example, digesting clones with appropriate restriction endonucleases and joining the fragments enzymatically in the proper orientation. Depending on the fragments and the particular restriction endonucleases chosen, it may be necessary to remove unwanted DNA sequences through a "loop out" process of deletion mutagenesis or through a combination of restriction endonuclease cleavage and mutagenesis. It is preferred that the resultant sequence be in the form of a continuous open reading frame, that is, that it lack intervening sequences (introns). The sequence of one exemplary human prostate clone described herein is shown in SEQ. ID. NO.14.

With the nucleotide and deduced amino acid sequences of human prostate transglutaminase provided herein, genomic or cDNA sequences encoding human prostatic transglutaminase may be obtained from libraries prepared from other cells and tissues according to known procedures. For instance, using oligonucleotide probes derived from human prostate transglutaminase sequences, generally of at least about fourteen nucleotides and up to twenty-five or more nucleotides in length, DNA sequences encoding transglutaminases of other cells or tissues may be obtained. If partial clones are obtained, it is necessary to join them in proper reading frame to produce a full length clone, using such techniques as endonuclease cleavage, ligation and loopout mutagenesis.

For expression, a DNA sequence encoding human prostate or placental transglutaminase polypeptide is inserted into a suitable expression vector, which in turn is used to transform or transfect appropriate host cells for expression. Expression vectors for use in carrying out the present invention will generally comprise a promoter capable of directing the transcription of a cloned DNA and a transcriptional terminator, operably linked with the sequence encoding the prostate or placental transglutaminase polypeptide so as to produce a continuously transcribable gene sequence which produces sequences in reading frame and is continuously translated to produce a human prostate or placental transglutaminase polypeptide. The expression vectors of the present invention may further include enhancers and other elements such as secretory signal sequences to facilitate expression and/or secretion of the protein. One or more selectable markers may also be included.

Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptides from the mature proteins as they pass through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

The choice of a suitable secretory signal sequence is well within the level of ordinary skill in the art and will depend on the selected host system employed. Preferred secretory signals include the a factor signal sequence (prepro sequence: Kurjan and Herskowitz, Cell 30: 933–943, 1982; Kurjan et al., U.S. Pat. No. 4,546,082; Brake, U.S. Pat. No. 4,870,008), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlsen et al., Molecular and Cellular Biology 3: 439–447, 1983), the α-1-antitrypsin signal sequence (Kurachi et al., Proc. Natl. Acad. Sci. U.S.A. 78: 6826–6830, 1981), and the α-2 plasmin inhibitor signal sequence (Tone et al., J. Biochem. (Tokyo) 102:1033–1042, 1987). A particularly preferred signal sequence is the tissue plasminogen activator signal sequence (Pennica et al., Nature 301: 214–221, 1983). Alternately, a secretory signal sequence may be synthesized according to the rules established, for example, by von Heinje (European Journal of Biochemistry 133: 17–21, 1983; Journal of Molecular Biology 184: 99–105, 1985; Nucleic Acids Research 14: 4683–4690, 1986).

Secretory signal sequences may be used singly or may be combined. For example, a first secretory signal sequence may be used in combination with a sequence encoding the third domain of barrier (described in U.S. Pat. No. 5,037,243, which is incorporated by reference herein in its entirety). The third domain of barrier may be positioned in proper reading frame 3' of the DNA segment of interest or 5' to the DNA segment and in proper reading frame with both the secretory signal sequence and a DNA segment of interest.

Host cells for use in practicing the present invention include mammalian, avian, plant, insect, bacterial and fungal cells, but preferably eukaryotic cells. Preferred eukaryotic cells include cultured mammalian cell lines (e.g., rodent or human cell lines) and fungal cells, including species of yeast (e.g., Saccharomyces spp., particularly S. cerevisiae, Schizosaccharomyces spp., or Kluyveromyces spp.) or filamentous fungi (e.g., Aspergillus spp., Neurospora spp.). Methods for producing recombinant proteins in a variety of prokaryotic and eukaryotic host cells are generally known in the art.

Suitable yeast vectors for use in the present invention include YRp7 (Struhl et al., Proc., Natl. Acad. Sci. U.S.A. 76: 1035–1039, 1978), YEp13 (Broach et al., Gene 8: 121–133, 1979), POT vectors (Kawasaki et al, U.S. Pat. No. 4,931,373, which is incorporated by reference herein), pJDB249 and pJDB219 (Beggs, Nature 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., Gene 8: 17, 1979), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., J. Biol. Chem. 255: 12073–12080, 1980; Alber and Kawasaki, J. Mol. Appl. Genet. 1: 419–434, 1982; Kawasaki, U.S. Pat. No. 4,599, 311) or alcohol dehydrogenase genes (Young et al., in Genetic Engineering of Microorganisms for Chemicals, Hollaender et al., (eds.), p. 355, Plenum, New York, 1982; Ammerer, Meth. Enzymol. 101: 192–201, 1983). In this regard, particularly preferred promoters are the TPI1 promoter (Kawasaki, U.S. Pat. No. 4,599,311, 1986) and the ADH2-4$^c$ promoter (Russell et al., Nature 304: 652–654, 1983; Irani and Kilgore, U.S. patent application Ser. No. 07/631,763 and EP 284,044, which are incorporated herein by reference). The expression units may also include a transcriptional terminator. A preferred transcriptional terminator is the TPI1 terminator (Alber and Kawasaki, ibid.).

Additional vectors, promoters and terminators for use in expressing the transglutaminases of the invention in yeast are well known in the art and are reviewed by, for example, Emr, Meth. Enzymol. 185:231–279, (1990), incorporated herein by reference.

The transglutaminases of the invention may be expressed in Aspergillus spp. (McKnight and Upshall, described in U.S. Pat. No. 4,935,349, which is incorporated herein by reference). Useful promoters include those derived from Aspergillus nidulans glycolytic genes, such as the ADH3 promoter (McKnight et al., EMBO J. 4:2093–2099, 1985) and the tpiA promoter. An example of a suitable terminator is the ADH3 terminator (McKnight et al., ibid.).

Techniques for transforming fungi are well known in the literature, and have been described, for instance, by Beggs (ibid.), Hinnen et al. (Proc. Natl. Acad. Sci. U.S.A. 75: 1929–1933, 1978), Yelton et al. (Proc. Natl. Acad. Sci. U.S.A. 81: 1740–1747, 1984), and Russell (Nature 301: 167–169, 1983). The genotype of the host cell will generally contain a genetic defect that is complemented by the selectable marker present on the expression vector. Choice of a particular host and selectable marker is well within the level of ordinary skill in the art.

In addition to fungal cells, cultured mammalian cells may be used as host cells within the present invention. Preferred cultured mammalian cells for use in the present invention include the COS-1 (ATCC CRL 1650) and BALB/c 3T3 (ATCC CRL 163) cell lines. In addition, a number of other mammalian cell lines may be used within the present invention, including BHK (ATCC CRL 10314), 293 (ATCC CRL 1573), Rat Hep I (ATCC CRL 1600), Rat Hep II (ATCC CRL 1548), TCMK (ATCC CRL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, Proc. Natl. Acad. Sci U.S.A. 77: 4216–4220, 1980).

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., Cell 41: 521–530, 1985), the SV40 promoter (Subramani et al., Mol. Cell. Biol. 1: 854–864, 1981), and the major late promoter from Adenovirus 2 (Kaufman and Sharp, Mol. Cell. Biol. 2: 1304–1319, 1982). Cellular promoters include the mouse metallothionein-1 promoter (Palmiter et al., U.S. Pat. No. 4,579,821), a mouse $V_K$ promoter (Bergman et al., Proc. Natl. Acad. Sci. U.S.A. 81: 7041–7045, 1983; Grant et al., Nuc. Acids Res. 15: 5496, 1987) and a mouse $V_H$ promoter (Loh et al., Cell 33: 85–93, 1983). Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., Nuc. Acids

*Res.* 9: 3719–3730, 1981). Vectors can also include enhancer sequences, such as the SV40 enhancer and the mouse μ enhancer (Gillies, *Cell* 33: 717–728, 1983). Expression vectors may also include sequences encoding the adenovirus VA RNAs. Vectors can be obtained from commercial sources (e.g., Stratagene, La Jolla, Calif.).

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973), electroporation (Neumann et al.,*EMBO J.* 1: 841–845, 1982), DEAE-dextran mediated transfection (Ausubel et al., (ed.) *Current Protocols in Molecular Biology,* John Wiley and Sons, Inc., N.Y. (1987), incorporated herein by reference) or a commercially available transfection regent and method such as the Boehringer Mannheim Transfection-Reagent N-[1-(2,3-Dioleoyloxy)propyl]-N,N,N-trimethyl ammoniummethyl-sulfate (Boehringer Mannheim, Indianapolis, Ind.). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology,* Butterworth Publishers, Stoneham, Mass., which is incorporated herein by reference). The choice of selectable markers is well within the level of ordinary skill in the art.

Selectable markers may be introduced into the cell on a separate vector at the same time as the transglutaminase sequence of interest, or they may be introduced on the same vector. If on the same vector, the selectable marker and the transglutaminase sequence of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods for introducing expression vectors encoding transglutaminase into plant, avian and insect cells are well known in the art. The use of baculoviruses, for example, as vectors for expressing heterologous DNA sequences in insect cells has been reviewed by Atkinson et al. (*Pestic. Sci.* 28: 215–224,1990). The use of *Agrobacterium rhizogenes* as vectors for expressing genes in plant cells has been reviewed by Sinkar et al. (*J. Biosci. (Banglaore)* 11: 47–58, 1987).

Host cells containing DNA constructs of the present invention are then cultured to produce the transglutaminase. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct by, for example, drug selection or deficiency in an essential nutrient which is complemented by the selectable marker on the DNA construct or co-transfected with the DNA construct.

Yeast cells, for example, are preferably cultured in a medium which comprises a nitrogen source (e.g., yeast extract), inorganic salts, vitamins and trace elements. The pH of the medium is preferably maintained at a pH greater than 2 and less than 8, preferably at pH 5–6. Methods for maintaining a stable pH include buffering and constant pH control, preferably through the addition of sodium hydroxide. Preferred buffering agents include succinic acid and Bis-Tris (Sigma Chemical Co., St. Louis, Mo.). Cultured mammalian cells are generally cultured in commercially available serum-containing or serum-free media. Selection of a medium appropriate for the particular cell line used is within the level of ordinary skill in the art.

In a preferred embodiment, the human prostate and placental transglutaminases are expressed in yeast as intracellular products. The yeast host can be a diploid strain homozygous for pep4, a mutation that reduces vacuolar protease levels, as described in Jones et al., *Genetics* 85:23–33 (1977), incorporated herein by reference. The strain is also homozygous for disruption of the endogenous TPI (triose phosphate isomerase) gene, thereby allowing the *S. pombe* POT1 gene to be used as a selectable marker. The vector includes the POT1 marker, a leu2-d marker and the ADH2-4$^c$ promoter. The POT1 marker in the TPI$^-$ host allows for selection by growth in glucose. The host strain is grown in glucose-containing synthetic media with a glucose feed. An ethanol feed is then substituted for glucose to de-repress the promoter. The pH is maintained with NaOH. Other preferred means for expression are generally described in, e.g., EPO publication EP 268,772, incorporated herein by reference.

In another preferred embodiment, the human prostate and placental transglutaminases are expressed in cultured mammalian cells. Preferably, the cultured mammalian cells are BHK 570 cells (deposited with the American Type Culture Collection under accession number 10314).

The human prostate and placental transglutaminases produced according to the present invention may be purified by affinity chromatography on an antibody column using antibodies directed against the transglutaminases. Additional purification may be achieved by conventional chemical purification means, such as liquid chromatography, gradient centrifugation, and gel electrophoresis, among others. Methods of protein purification are known in the art (see generally, Scopes, R., *Protein Purification,* Springer-Verlag, NY (1982), which is incorporated herein by reference) and may be applied to the purification of the recombinant transglutaminase described herein. Antibodies prepared against the novel transglutaminases may be either polyclonal or monoclonal, and can be used to isolate and substantially purify the recombinant or native transglutaminases of the invention. Substantially pure recombinant human prostatic or placental transglutaminase of at least about 50% is preferred, at least about 70–80% more preferred, and 95–99% or more homogeneity most preferred, particularly for pharmaceutical uses. Once purified, partially or to homogeneity, as desired, the recombinant or native human prostatic and placental transglutaminases described herein may be used as desired.

The human prostatic and placental transglutaminases produced according to the present invention find a variety of uses. These transglutaminases can be used therapeutically in humans or other mammals. For example, human transglutaminase may be used in the repair of wounds, ulcerated lesions, skin grafts, etc. As the human transglutaminases are relatively stable, active extracellularly, and bind avidly to collagen, they can be used to stabilize basement membrane structures. An appropriate endogenous substrate for transglutaminase is fibronectin, which thus serves as a basis for crosslinking and stabilizing collagen/fibronectin complexes.

Pharmaceutical compositions of the invention comprise therapeutically effective amounts of human prostatic and/or placental transglutaminase and an appropriate physiologically acceptable carrier. The pharmaceutical compositions are intended primarily for topical or local administration, for use in methods of wound closure, as tissue adhesives, and the like. Typically the transglutaminase will be administered concurrently with or prior to compositions of thrombin to the wound site to increase effectiveness.

A variety of aqueous carriers may be used in the compositions, e.g., water, buffered water, saline, 0.3% glycine and the like, including glycoproteins for enhanced stability, such as albumin, lipoprotein, fibronectin and/or globulin. The compositions may be sterilized by well known sterilization techniques, and the solutions packaged for use or lyophilized. Other components of the pharmaceutical compositions of the invention can include pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

Other components may also be added to the transglutaminase compositions to enhance their effectiveness, such as calcium ions, protease inhibitors (e.g., aprotinin), fibrinogen, etc. Admixtures of prostaglandins, coagulation factors, antihistamines, vasopressins, growth factors, vitamins, antibiotics (e.g., aminoglycosides, penicillins, carbapenems, sulfonamides, tetracyclines) and the like may also be provided. The formulation of various wound tissue adhesives is discussed in detail in U.S. Pat. Nos. 4,427,650, 4,442,655, and 4,655,211, each of which is incorporated herein by reference.

The concentration of human prostatic and/or placental transglutaminase in the pharmaceutical formulations can vary widely, i.e., from about 20 μg/ml to 20 mg/ml or more, usually at least about 50 μg to 1 mg/ml, preferably from about 100 μg to 500 μg/ml and will be selected primarily by volumes, viscosities, strength of the resulting complex, etc., in accordance with the particular use intended, the severity of the wound, the mode of administration selected, etc. Amounts effective for these uses will depend on the severity of the wound, injury or disease and the general state of the patient, but generally range from about 100 μg to about 500 mg or more of transglutaminase per site, with dosages of from about 500 μg to about 50 mg of transglutaminase per site being more commonly used. It must be kept in mind that the materials of the present invention may generally be employed in serious disease or injury states, that is, life-threatening or potentially life threatening situations. In such cases, in view of the minimization of extraneous substances, decreased immunogenicity and the prolonged half-life and stability of the human prostatic and placental transglutaminases made feasible by this invention, it is possible and may be felt desirable by the treating physician to administer substantial excesses of these transglutaminase compositions.

The transglutaminases described herein can also be used in the preparation of food material, such as paste food or cheese, and can be added to dehydrated fish to prevent deterioration caused by protozoans, e.g., myxamoeba. The transglutaminases can also be used in the preparation of ground meat of okiomi (*Euphasia superba*), by adding to dehydrated meat parts from 0.1 to 100 units, preferably about 1–40 U per gram of protein to improve meat texture and quality. Frozen granular meats can be improved by combining meat material with transglutaminase of the invention at 1–500 U per gram protein, at 30–60° C. for 10–120 min. to promote crosslinking between glutamine groups and lysine contained in meat preparations.

Other uses of the human prostatic and placental transglutaminases described herein include use in the enzyme-catalyzed labeling of proteins and cell membranes (Iwanij, *Eur. J. Biochem.* 80:359–368 (1977), incorporated herein by reference), in the introduction of cleavable crosslinks, and in the solid phase reversible removal of specific proteins from biological systems.

Transglutaminase expression can be used as a marker for screening for agonists and antagonists of cellular apoptosis. Identifying agents which inhibit the expression of transglutaminase by a cell provides a means to prevent or delay atrophic changes characteristic of many degenerative changes, particularly degenerative nerve diseases, such as Parkinson's disease and Alzheimer's disease. Inhibition of apoptosis may also enhance blood cell counts in chemotherapy patients. The human prostatic and placental transglutaminase or the nucleic acids which encode the transglutaminases of the invention can also be used to identify agents which induce apoptotic activity by a cell, for the control of, e.g., hyperproliferative disorders. The growth of cells such as adipocytes can be regulated with agents identified using the transglutaminases provided herein as a marker, providing a means for controlling fat deposits in certain forms of obesity without the necessity for surgical intervention.

Polynucleotide molecules which encode the prostatic and placental transglutaminases may be directly detected in cells with labeled synthetic oligonucleotide probes in a hybridization procedure similar to the Southern or dot blot. Also, PCR (including Saiki et al., *Science* 239:487 (1988)) may be used to amplify DNA sequences, which are subsequently detected by their characteristic size on agarose gels, Southern blots of the gels using transglutaminase sequences or oligonucleotide probes, or a dot blot using similar probes. The probes of the present invention are at least 85% homologous to a corresponding DNA sequence of a human prostate transglutaminase sequence of Sequence ID No. 14 or its complement or a human placental transglutaminase sequence of Sequence ID No. 22 or its complement. For use as probes, the molecules may comprise from about 14 nucleotides to about 25 or more nucleotides, sometimes 40 to 60 nucleotides, and in some instances a substantial portion or even the entire cDNA of a transglutaminase gene of the invention may be used. The probes are labeled to provide a detectable signal, such as an enzyme, biotin, a radionuclide, fluorophore, chemiluminescer, paramagnetic particle, etc.

The following examples are provided by way of illustration, not limitation.

EXAMPLE I

Cloning of Human Prostatic Transglutaminase

This Example describes the construction of oligonucleotide primers for amplification via PCR of sequences encoding human prostate transglutaminase, the cloning of the human prostate transglutaminase gene, and its nucleotide sequencing.

A series of synthetic degenerate oligonucleotide primers were generated to encode three regions of conserved amino acid sequences identified from a multiple alignment of known transglutaminase sequences, human erythrocyte membrane protein band 4.2 and the rat dorsal protein-1 (Ho et al., *Prog. Clin. Biol. Res.* 239: 125–153, (1987)). The multiple alignment employed sequences of rat keratinocyte transglutaminase, human keratinocyte transglutaminase, human transglutaminase K, human factor XIII, human endothelial cell transglutaminase, mouse macrophage transglutaminase, guinea pig transglutaminase, human erythrocyte membrane protein band 4.2, rabbit transglutaminase type I, and bovine factor XIII. The multiple alignment was subjected to analysis of subsequence for least degenerate/most conserved regions to design primers of 17–20 bases in length. The amino acid sequences across three regions of multiple homology were chosen as the basis from which to design degenerate primers: One region corresponding to the active site region of factor XIII, and two other regions which seemed to have structural importance, based on, inter alia, the presence of hydrophobic residues and proline residues. Degenerate oligonucleotides ZC4109, ZC4110, ZC4111 and ZC4112 (Sequence ID Nos. 1, 2, 3 and 4) were designed to provide DNA segments corresponding to the conserved amino acid coding sequences. Degenerate oligonucleotides ZC4120, ZC4121, ZC4122, ZC4127, ZC4128, and ZC4129 (Sequence ID Nos. 5, 6, 7, 8, 9 and 10; Table 1) were designed such that each primer contained a 5' prime sequence to facilitate cloning into prime vectors described by Hagen (U.S. Pat. No. 5,075,227, incorporated herein by reference) in addition to a DNA segment corresponding to the conserved amino acid coding sequence. The prime sequences shown in Table 1 are underlined.

TABLE 1

Degenerate Oligonucleotide Primers (5' to 3')

ZC4120 (Sequence ID Number 5)
CATCCACGGA CTACGACGAR TAYSTNCTNA MYGA

ZC4121 (Sequence ID Number 6)
CATCCACGGA CTACGACGAR TAYSTNCTNA MRGA

ZC4122 (Sequence ID Number 7)
CATCCACGGA CTACGACGAR TAYSTNCTNA MNCA

ZC4127 (Sequence ID Number 8)
CATCCACGGA CTACGACTAY GGNCARTGY TGGGTNTT

ZC4128 (Sequence ID Number 9)
ACTCTCCGGT ACGACAGAAN ACCCARCAYT GNCC

ZC4128 (Sequence ID Number 10)
ACTCTCCGGT ACGACAGCCY TCNKGRWRYT TRTA

The oligonucleotide primers were paired as shown in Table 2, and each pair was used in a PCR reaction using a λgt11 human prostate tissue cDNA library obtained from Clontech Laboratories, Inc., Palo Alto, Calif. as a template. Fifty microliter reactions were set up with each reaction containing 0.2 mM each of dCTP, dGTP, dATP and dTTP, 2 pmol of each primer, 1 μl of the cDNA library, 3 units of Taq polymerase (Promega Corp., Madison, Wis.) and 5 μl of 10x Promega PCR buffer (Promega Corp., Madison, Wis.). The reactions were each overlaid with mineral oil and amplified with two cycles (90 seconds at 94° C., 90 seconds at 40° C., 2 minutes at 72° C.), thirty-eight cycles (45 seconds at 94° C., 45 seconds at 45° C., two minutes at 72° C.) and an incubation at 72° C. for seven minutes.

TABLE 2

Oligonucleotide Primer Combinations And Expected Fragment Sizes (Base Pairs)

| RXN | SENSE OLIGO | ANTISENSE OLIGO | EXPECTED FRAGMENT SIZE |
|---|---|---|---|
| 1. | ZC4110 | ZC4112 | 344 |
| 2. | ZC4110 | ZC4111 | 851 |
| 3. | ZC4109 | ZC4111 | 527 |
| 4. | ZC4127 | ZC4129 | 561 |
| 5. | ZC4120 | ZC4128 | 378 |
| 6. | ZC4121 | ZC4128 | 378 |
| 7. | ZC4122 | ZC4128 | 378 |
| 8. | ZC4120 | ZC4129 | 885 |
| 9. | ZC4121 | ZC4129 | 885 |
| 10. | ZC4122 | ZC4129 | 885 |

Aliquots of the reaction mixtures were electrophoresed on an agarose gel. Reactions 3, 4 and 6 exhibited bands of expected size (527 bp, 561 bp and 378 bp, respectively). The PCR reaction products were isolated by agarose gel electrophoresis, and the DNA fragments were extracted with a Bio-Rad PREP-A-GENE kit (Bio-Rad, Richmond, Calif.) using the manufacturer's directions. The purified fragments were ligated into pCR1000 (Invitrogen, San Diego, Calif.) from the TA Cloning Kit (Invitrogen) and transformed into *E. coli* strain INVaF' (Invitrogen) using the manufacturer's protocol (Invitrogen TA Cloning Instruction Manual K2000-1). Two clones from PCR reaction 4, designated PTG561/1 and PTG561/2, were selected for subsequent analysis. Sequence analysis of the PCR-generated cDNA inserts in plasmids PTG561/1 and PTG561/2 showed that PTG561/2 (SEQ. ID. NO. 13) contained a unique sequence.

To generate a full-length prostate transglutaminase cDNA clone, sense and antisense oligonucleotide primers were designed to specific sequences in the PTG561/2 clone. Oligonucleotides ZC4248 and ZC4249 (Sequence ID Nos. 11 and 12) were used to amplify a 468 base pair fragment from clone PTG561/2 that was used to probe the prostate cDNA library. A fifty microliter reaction mixture was set up containing 2 pmols each of ZC4248 and ZC4249, 0.025 mM dGTP, 0.025 mM dTTP, $6.6 \times 10^{-3}$ mM $\alpha$-$^{32}$P dCTP, $6.6 \times 10^{-3}$ mM $\alpha$-$^{32}$P dATP, 1xPromega PCR buffer, 1 μl of purified plasmid diluted 1:100 and 0.5 μl Taq polymerase. The reaction mixture was layered with mineral oil, and the mixture was preheated for approximately three minutes at 87° C. The reaction was amplified for six cycles (one minute at 94° C., one minute at 45° C., one minute at 72° C.) and one incubation at 72° C. for five minutes. A 45 μl aliquot of the amplified reaction mixture was isopropanol precipitated, and the radiolabeled PCR product was used to probe the λgt11 human prostate cDNA library (Clontech). Six positive clones were selected for further analysis.

The six clones were subjected to PCR amplification using oligonucleotides ZC4362 and ZC4363 (Sequence ID Nos. 19 and 20, respectively), which were designed to anneal to sequences in the λgt11 vector, to characterize the cDNA inserts. Six 50 μl reaction mixtures were prepared, each of which contained 1 μl of a plate lysate of one of the selected clones, 1xPromega PCR buffer, 0.2 mM of each dNTP, 2 pmole each of ZC4362 and ZC4363 (Sequence ID Nos. 19 and 20, respectively), and 3 units of Taq polymerase. The reactions were overlaid with mineral oil, and the mixtures were pre-heated to 94° C. for two minutes to disrupt the phage. The reactions were amplified through 30 cycles (1 minute at 94° C., 1 minute at 50° C., three minutes at 72° C.) followed by one cycle at 72° C. for 7 minutes. The reaction products were isolated by agarose gel electrophoresis, and each reaction product was subcloned into PCR1000 (Invitrogen, San Diego, Calif.) and transformed into E. coli strain INVαF' (Invitrogen) using the TA cloning kit (Invitrogen).

One of the six lambda clones, 8c2, was selected for sequence analysis. Lambda DNA was prepared from the 8c2 clone, and the cDNA insert was isolated as an Eco RI fragment and subcloned into Eco RI-linearized pUC18 to obtain plasmid pDT43. The 8c2 cDNA insert was subjected to DNA sequence analysis. Based on homology with a published rat prostate protein sequence (Ho et al., J. Biol. Chem. 267: 12660–12667, 1992), it was determined that the prostate transglutaminase clone 8c2 lacked the 5' coding sequence.

To confirm the presence of additional 5' sequences, the original six lambda clones were used as templates for PCR reactions using oligonucleotides ZC5509 (Sequence ID No. 21) and ZC4048 (Sequence ID No. 18). Each reaction mixture contained 1×PCR buffer, 1.25 MM $MgCl_2$, 0.2 mM of each dNTP, 20 μM ZC5509, 17.5 μl of 20 μM ZC4048, 1.5 units of Taq polymerase. The reaction mixture was divided into 24 μl aliquots. Each aliquot received 1 μl of template, and the reaction mixtures were amplified for thirty cycles (94° C. for one minute, 42° C. for one minute, 72° C. for two minutes) followed by a seven minute incubation at 72° C. The reaction mixtures were subjected to agarose gel electrophoresis. Analysis of the PCR products showed that clones 11A2 and 11A3 generated the largest PCR products relative to clone 8c2, suggesting that these two clones contained additional 5' prostate transglutaminase coding sequences.

The 5' human prostate coding sequence was obtained by amplification from the two lambda clones (11A2 and 11A3) described above. Synthetic oligonucleotide ZC4048 (Sequence ID No. 18) was designed to hybridize to the antisense lambda sequences near the Eco RI site of the λgt11 vector. Synthetic oligonucleotide ZC5509 (Sequence ID No. 21) was designed to hybridize to the sense sequences in the 5' coding sequence of the PTG561/2 cDNA (Sequence ID No. 13).

Two 50 μl reaction mixture were prepared containing 9.3 μl of either 11A2 or 11A3 phage from plate lysates, 5 μl 10×Promega PCR buffer, 5 μl of a solution containing 0.2 mM of each dNTP, 2.5 μl each of 20 pMol/μl ZC4048 and 20 pMol/μl ZC5509 (Sequence ID Nos. 18 and 21, respectively), 25.1 μl of water and 0.6 μl of Taq polymerase. The reactions were incubated at 94° C. for two minutes to disrupt the phage followed by thirty cycles (45 seconds at 94° C., 45 seconds at 42° C., 90 seconds at 72° C.). After the final amplification cycle, the reactions were incubated at 72° C. for five minutes. The reactions were subjected to agarose gel electrophoresis, and an approximately 530 bp band was isolated from each reaction. The PCR-generated fragments were subcloned into pCRII (Invitrogen, San Diego, Calif.) using the manufacturer's supplied instructions. Sequence analysis of several clones showed identical sequences spanning the λgt11 Eco RI cloning site and sequences present in the 8c2 clone. One clone, pDT46-1 was selected for further manipulation.

The 5' transglutaminase coding sequence present in pDT46-1 but missing from the 8c2 clone was obtained by digesting pDT46-1 with Spe I and Ava I to isolate the 351 bp fragment. The 3' transglutaminase coding sequence was obtained by digesting plasmid pDT43 with Ava I and Xba I and isolating the fragment containing the transglutaminase and vector sequences. The Spe I and Xba I digestion produce complementary adhesive ends. The Spe I-Ava I fragment from pDT46-1 and the Ava I-Xba I fragment from pDT43 were ligated to obtain plasmid pDT47-15, which contained the prostate transglutaminase coding sequence of Sequence ID No. 14.

EXAMPLE II

Expression of Human Prostate Transglutaminase
This Example describes the expression of a human prostate transglutaminase from cultured mammalian cells.

The prostate transglutaminase cDNA insert present in plasmid pDT47-15 was subcloned into the mammalian expression vector Zem229R. Plasmid Zem229 is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene, and SV40 terminator. Zem229 was modified to delete the two Eco RI sites by partial digestion with Eco RI, blunting with DNA polymerase I (Klenow fragment) and dNTPs, and re-ligation. Digestion of the resulting plasmid with Bam HI followed by ligation of the linearized plasmid with Bam HI-Eco RI adapters resulted in a unique Eco RI cloning site. The resultant plasmid was designated Zem229R.

Plasmid pDT47–15 was digested with Hind III to isolate the approximately 3 kb Hind III fragment containing the prostate transglutaminase cDNA. Synthetic oligonucleotides ZC1157 and ZC1158 (Sequence ID Nos. 16 and 17, respectively) were kinased and annealed to form Eco RI-Hind III adapters. The kinased, annealed oligonucleotides and the 3 kb Hind III fragment were ligated to Eco RI-linearized Zem229R. The ligation mixture was transformed into E. coli strain DH10B cells, and transformants were selected for growth in the presence of ampicillin. Plasmid DNA prepared from selected transformants was subjected to restriction endonuclease analysis. A plasmid clone, pPTG/229R, suspected of having the insert in the correct orientation relative to the promoter, was selected for DNA sequence analysis to confirm the orientation of the insert. DNA sequence analysis confirmed the orientation of the insert and also disclosed the presence of polylinker sequences between the promoter sequence of Zem229R and the beginning of the prostate transglutaminase coding sequence. These sequences appeared to be remnants from the initial cloning procedure.

The polylinker sequences between the promoter sequence of Zem229R and the prostate transglutaminase coding sequence were removed by first digesting plasmid pPTG/229R with Eco RI to completion. The approximately 236 base pair fragment containing the 5'-most transglutaminase coding sequence and the approximately 2.7 kb fragment containing the remainder of the transglutaminase coding sequence were isolated by agarose gel electrophoresis. The two Eco RI fragments were ligated with Eco RI-linearized Zem229R that had been treated with calf alkaline phosphatase to prevent recircularization. The ligation mixture was transformed into E. coli strain DH10B cells, and transformants were selected in the presence of ampicillin. Plasmid DNA prepared from selected transformants was analyzed by restriction enzyme analysis. A plasmid containing the prostate transglutaminase cDNA insert in the proper orientation relative to the promoter in Zem229R was designated pPTGR/229R.

Both plasmids pPTG/229R and pPTGR/229R were transfected into BHK 570 cells (deposited with the American Type Culture Collection under accession number 10314) using Boehringer Mannheim Transfection-Reagent N-[1-(2, 3-Dioleoyloxy)propyl]-N,N,N-trimethyl ammoniummethyl-sulfate using the manufacturer-supplied directions. The cells were cultured under non-selective conditions for two days. After two days the pPTG/229R transfectants were selected in media containing 1 μM methotrexate, and the pPTGR/229R transfectants were selected in media containing either 1 μM or 10 μM methotrexate.

Transfectant colonies were overlaid with a nitrocellulose filter, and the colonies were incubated for 3 hours. After incubation, the filter was lifted and probed with rabbit anti-rat prostate transglutaminase antiserum, obtained from Dr. V. Gentile (University of Texas-Medical School, Houston, Tex.). The filters were incubated with a peroxidase-conjugated goat anti-rabbit IgG, and colonies bound by the rabbit anti-rat prostate transglutaminase antibodies were visualized using the chemiluminescent ECL REAGENT (Amersham Corp., Arlington Heights, Ill.) using the manufacturer's instructions. Six positive pPTG/229R transfectant colonies were each picked into a well of a 24-well plate. Of the pPTGR/229R transfectant colonies, 12 positive colonies were picked from those colonies selected in the presence of 1 μM methotrexate, and 12 positive colonies were picked from those colonies selected in the presence of 10 μM methotrexate.

The colonies are subjected to in vivo labeling followed by radioimmunoprecipitation of the protein with the rabbit anti-rat prostate transglutaminase antiserum. Briefly, the medium in each well is replaced with 1 ml of serum-free medium (DMEM-Lys-Met, 1 mM sodium pyruvate, 2 mM L-glutamine, 5 mg/l insulin, 2 μg/l selenium, 10 mg/l fetuin, 10 mg/l transferrin and 25 mM pH 7.2 HEPES buffer) containing 20 μCi of $^{35}$S-EXPRESS (Du Pont-NEN Research Products, Boston, Mass.), and the cells are incubated overnight at 37° C. After incubation, 1 ml of each supernatant is harvested, and the cells are rinsed with PBS. Cell extracts from each culture are obtained by incubating the cells with 1 ml RIPa buffer (10 mM Tris, pH 7.4, 1% deoxycholate, 1% Triton X-100, 0.1% SDS, 5 mM EDTA, 0.7 M NaCl). The labeled proteins are incubated with a 1:300 dilution of rabbit anti-rat prostate transglutaminase antiserum on ice for one hour. After incubation, 10 μl of PANSORBIN (S. aureus cells, Calbiochem, San Diego, Calif.) is added to each reaction, and the mixtures are incubated on ice for one hour. The reactions are centrifuged, and the pellets are resuspended in 1 ml of RIP wash buffer (0.1% SDS, 5 mM EDTA, 0.7 M NaCl). The reactions are centrifuged, the pellets are each resuspended in 20 μl of loading buffer and the samples are applied to a 10/20 gradient polyacrylamide gel (Daichi). The gel is fixed for thirty minutes in 40% methanol, 10% acetic acid, following which the gel is incubated in AMPLIFY (Amersham) for 30 minutes. The gel is dried and exposed to film at −80° C. The autoradiograph is examined to identify the presence of prostate transglutaminase.

EXAMPLE III

Cloning of Human Placental Transalutaminase

This Example describes the cloning of a human placental transglutaminase from human placental cDNA and identification of a confirmatory human prostatic transglutaminase clone from human liver cDNA.

Two other cDNA sources were used in conjunction with selected degenerate oligonucleotide primers described in Example I to obtain unique transglutaminase cDNAs. QUICK-CLONE human liver cDNA (Clontech) and QUICK-CLONE human placenta cDNA (Clontech) were used as templates with oligonucleotide primers paired as shown in Table 3. Fifty microliter reactions were set up with each reaction containing 0.2 mM each of dCTP, dGTP, DATP and dTTP, 2 pmol of each primer, 1 μg of the cDNA library, 3 units of Taq polymerase (Promega Corp., Madison, Wis.) and 5 μl of 10×Promega PCR buffer (Promega Corp., Madison, Wis.). The reactions were layered with mineral oil and amplified with two cycles (90 seconds at 94° C., 90 seconds at 50° C., 2 minutes at 72° C.), twenty-five cycles (45 seconds at 94° C., 45 seconds at 55° C., one minute at 72° C.) and one incubation at 72° C. for seven minutes.

TABLE 3

Oligonucleotide Primer Combinations And Expected Fragment Sizes (Base Pairs)

| RXN | TEMPLATE | SENSE OLIGO | ANTISENSE OLIGO | EXP. FRAG. SIZE |
| --- | --- | --- | --- | --- |
| 1. | LIVER | ZC4127 | ZC4129 | 561 |
| 2. | | ZC4120 | ZC4128 | 378 |
| 3. | | ZC4121 | ZC4128 | 378 |
| 4. | | ZC4122 | ZC4128 | 378 |
| 5. | | ZC4120 | ZC4129 | 885 |
| 6. | | ZC4121 | ZC4129 | 885 |
| 7. | | ZC4122 | ZC4129 | 885 |
| 14. | PLACENTA | ZC4127 | ZC4129 | 561 |
| 15. | | ZC4120 | ZC4128 | 378 |
| 16. | | ZC4121 | ZC4128 | 378 |
| 17. | | ZC4122 | ZC4128 | 378 |
| 18. | | ZC4120 | ZC4129 | 885 |
| 19. | | ZC4121 | ZC4129 | 885 |
| 20. | | ZC4122 | ZC4129 | 885 |

Aliquots of the amplified DNA were electrophoresed on agarose gels. Reactions 1, 3, 14, 15, 16, and 17 yielded fragments of expected size (Table 3). The PCR-generated cDNA fragments were electrophoresed on agarose gels, and the fragments were extracted with a Bio-Rad PREP-A-GENE Kit (Bio-Rad, Richmond, Calif.) using the manufacturer's directions. The purified fragments were ligated into pCR1000 (Invitrogen, San Diego, Calif.) and transformed into E. coli strain INVaF' (Invitrogen) according to the TA Cloning Kit (Invitrogen) using the manufacturer's protocol (Invitrogen TA Cloning Instruction Manual K2000-1). Clones from reactions 1 and 14 were selected for subsequent analysis. Sequence analysis of a clone arising from reaction 1 revealed the same human prostatic transglutaminase sequence as found in PTG561/2. Sequence analysis of a clone arising from reaction 14 PCR cDNA, designated p1TG561/5, revealed a novel transglutaminase sequence. The nucleotide sequence of p1TG561/5 is shown in Sequence ID No. 22.

It is evident from the above results that compositions are provided which encode novel prostatic and placental human transglutaminases. Pharmaceutical preparations of these transglutaminases are particularly useful as wound tissue adhesives, in view of the minimization of extraneous substances when produced by recombinant means, decreased immunogenicity in humans and prolonged half-life and stability. The efficacy, convenience of administration, and reduced cost are among the advantages conferred by the compositions of the invention.

The transglutaminases described herein can also be used, inter alia, in the preparation of food material, in the enzyme-catalyzed labeling of proteins and cell membranes, as markers for screening for agonists and antagonists of cellular apoptosis, and for the detection or monitoring of expression in cells with labeled synthetic oligonucleotide probes or other convenient assays.

Although the foregoing invention has been described in some detail by way of illustration and example for purposes of clarity of understanding, it will be obvious that certain changes and modifications may be practiced within the scope of the appended claims.

What is claimed is:

1. A human placental transglutaminase polypeptide encoded by the nucleic acid sequence comprising the sequence of SEQ ID NO: 22 or an allelic variant thereof.

2. The polypeptide of claim 1, which catalyzes $Ca^{++}$-dependent crosslinking of protein-bound glutamine and lysine residues.

3. A pharmaceutical composition which comprises purified human placental transglutaminase polypeptide encoded by the nucleic acid sequence comprising the sequence of SEQ ID NO: 22 or an allelic variant thereof, and a pharmaceutically acceptable carrier.

4. A method for facilitating wound repair in a patient, which comprises administering the pharmaceutical composition of claim 3.

* * * * *